United States Patent [19]

van Heiningen

[11] Plant 5,075

[45] Jul. 26, 1983

[54] WILTON PYRAMIDAL HYBRID YEW TREE

[76] Inventor: Dirk van Heiningen, 6850 Carlisle Rd., Dover, Pa. 17315

[21] Appl. No.: 278,085

[22] Filed: Jun. 29, 1981

[51] Int. Cl.[3] ..... A01H 5/00

[52] U.S. Cl. ..... Plt./50

[58] Field of Search ..... Plt./50

[56] References Cited

U.S. PATENT DOCUMENTS

P.P. 1,617 7/1957 Hess ..... Plt./50

OTHER PUBLICATIONS

Ouden, P. D. et al., "*T. cuspidata*" *Manual of Cultivated Conifers,* Pub. Martinus Nijhoff, The Hague, Netherlands 1965, pp. 406–409.

*Primary Examiner*—James R. Feyrer

*Attorney, Agent, or Firm*—George L. Herr

[57] ABSTRACT

The tree of this invention is the 'Wilton Pyramidal Yew' which was derived from the chance pollination between the *Taxus cuspidata* and the *Taxus media 'Hatfield'*. It is a male plant and produces no seeds. It can be reproduced asexually only from terminal cuttings. The 'Wilton Pyramidal Yew' is a broad base tree with a limited number of terminal cuttings located only at the top of the tree. It has a relatively slow rate of growth, is of a rich green color, and the leaves extend well into the interior of the tree from the top to the base making it adaptable for deep pruning without uncovering bare branches.

1 Drawing Figure

1

This invention relates to a new and distinct variety of Yew Tree—*Taxus cuspidata 'Wilton Pyramid'*—known as 'Wilton Pyramidal Hybrid Yew'.

'Wilton Pyramidal Hybrid Yew' resulted from a chance pollination between the *Taxus cuspidata* and the *Taxus media 'Hatfield'*. It is a male plant producing no seed and can be reproduced asexually from only terminal cuttings. The chance pollination which first produced this tree took place at the Wholesale Nursery of the Evergreen Nursery Company at Wilton, Fairfield County, Conn. This nursery was owned and operated by applicant's father at the time of this development.

The yew tree of this invention was produced by the chance cross pollination of the *Taxus cuspidata* as described at page 406 in the Manual of Cultivated Conifers by P. Den Ouden and Dr. B. K. Boom (1965) and the *Taxus media 'Hatfield'* described at page 411 in the same publication. The two trees were growing in close proximity to one another at the nursery at Wilton, Conn.

The 'Wilton Pyramidal Yew' has several distinguishing features over the parent yews and the prior art. It is a broad based tree which gives it it's distinctive pyramidal shape rather than the columnar or cylindrical shape such as the yew disclosed in Hess U.S. Plant Pat. No. 1,617 made of record in this application. The yew of this invention has a limited number of terminal cuttings occurring at the top of the tree—usually about 3 to 5 cuttings per tree as contrasted with the prior art yews which have many terminal cuttings occurring throughout the height of the tree. While the yew of the invention has many lateral cuttings, these will not produce the broad based pyramidal yew of the invention.

The needles of the yew of the invention are distinctive in that they are 38 to 40 mm. in length at the base of the growth and 20 mm. in length at the tip. The needles project upwardly from the stem at an angle of approximately 45°. The annual growth of the plant is approximately 20 cm. at the van Heiningen Nurseries at Dover, York County, Pa. This is contrasted with a growth of about 30 cm. per year for the *Taxus cuspidata* at the same location. With this slow growth, pruning need not be as frequent as with the faster growing trees.

2

The color of the tree of the invention is a rich green color substantially the same as the *T. cuspidata* and the *'Hatfield'*. However, in the yew of the invention the color is uniform from top to bottom of the tree and the leaves extend farther into the interior of the plant than is the case of the parents. The yew of the invention holds its rich green color throughout cold weather while the parent trees assume a dull tone in cold weather.

The stem of the new growth of the yew of the invention is substantially the same rich green color as the leaves and it retains this green color well into the third year while the parent trees' stem turns to brown wood in the second year.

The 'Wilton Pyramidal Yew' is dioecious, male and it's flower is rather insignificant, but it occurs between the 1st and 15th of May at Dover, Pa. and sends out it's pollen for a period of two weeks. Since it is a male plant, it produces no fruit.

The bark of the tree is a reddish brown color and when it sheds, it becomes a lighter brown.

The illustration shows, in side view, a typical specimen of the plant.

The Plant:

*Type.*—Pyramidal Yew Tree.

*Form.*—Broad-based with branches extending upwardly at an angle of approximately 45°.

*Growth habit.*—Slow growing. Retains it's compact pyramidal shape requiring a minimum of pruning. Growth 20 cm. per year.

*Cold resistance.*—Is hardy and can be grown in southern Canada as well as the United States.

*Propagation.*—Can be reproduced only asexually from terminal cuttings of which only a few are produced at the top of the tree.

*Leaves.*—38 to 40 mm. at base of new growth and 20 mm. at tip, arranged uniformly around the stem 1/16" apart and extending outwardly from the stem at an angle of 45°.

*Flowers.*—Insignificant but appear between 1st and 15th of May at Dover, Pa.

The yew of this invention is distinctly different from the Hatfield and the Cuspidata in many ways:

1. It cannot be reproduced other than asexually.

2. It's growth rate is slower than either of it's parents.

3. It is much more compact.

4. Because of it's slow rate of growth, it requires fewer prunings during any given period of time.

5. It retains it's color throughout the year and does not dull in winter.

6. The color is uniform from top to bottom, including the lower branches which hug the ground.

7. The foliage clothes all the branches deep into the plant structure. This feature is very unique and desirable.

8. Propagation of the 'Wilton Pyramid' is by terminal cuttings in contrast to many columnare forms from terminal cuttings.

9. The Yew of this invention has the very attractive pyramidal shape illustrated in the accompanying drawing.

I claim:

1. A new and distinct variety of hybrid Yew substantially as herein shown and described, characterized particularly by it's novel shape and unique color and extent of foliage.

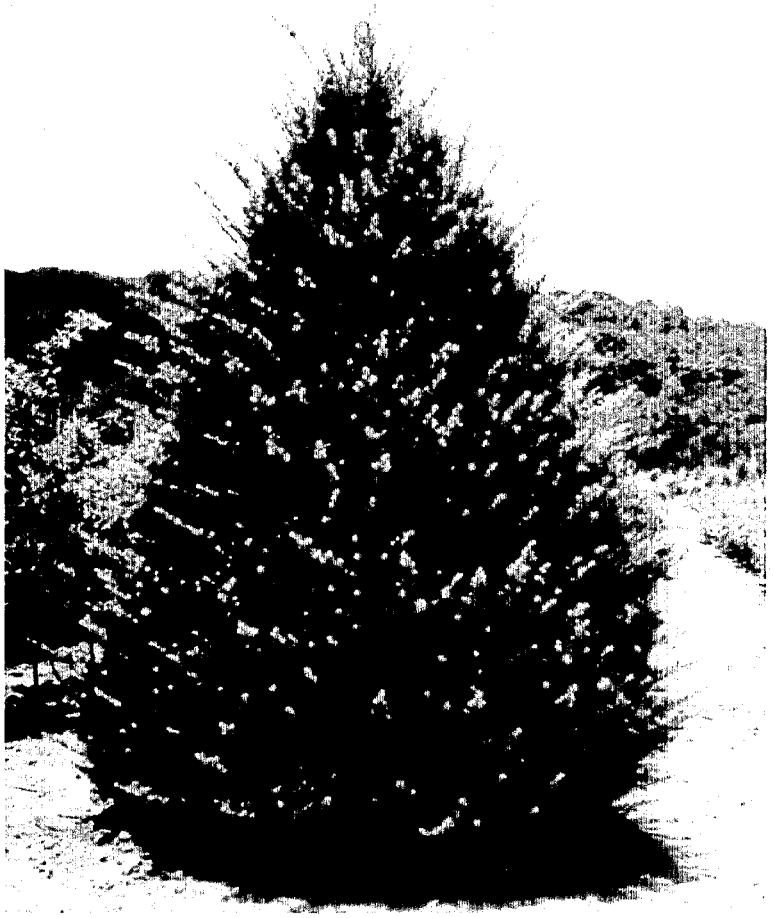

* * * * *